United States Patent [19]

Van Dijk et al.

[11] Patent Number: 5,074,296

[45] Date of Patent: Dec. 24, 1991

[54] RESPIRATING APPARATUS FOR PATIENTS

[76] Inventors: Geert Van Dijk, Wibautstraat 27, Maarssen; Bart Westerkamp, Klipperstraat 28, Alkmaar, both of Netherlands

[21] Appl. No.: 592,592

[22] Filed: Oct. 4, 1990

Related U.S. Application Data

[63] Continuation of Ser. No. 327,870, Mar. 23, 1989, abandoned.

[30] Foreign Application Priority Data

Mar. 23, 1988 [NL] Netherlands .................. 8800718

[51] Int. Cl.[5] .................................. A61M 15/00
[52] U.S. Cl. ........................ 128/200.24; 128/203.12

[58] Field of Search ............... 128/203.12–203.14, 128/203.16–203.19, 203.22, 203.25–203.27, 200.14, 200.24

[56] References Cited

U.S. PATENT DOCUMENTS 2,586,677  2/1952  Marrett ..................... 128/203.12
4,554,916  11/1985  Watt ......................... 128/203.12

Primary Examiner—Edgar S. Burr
Assistant Examiner—Aaron J. Lewis
Attorney, Agent, or Firm—Pollock, Vande Sande & Priddy

[57] ABSTRACT

Respirating apparatus for patients, formed by a housing which encloses means for forming and administering the respiratory gas, and in which the housing has the shape of a three sided prism or a cylinder sector.

5 Claims, 1 Drawing Sheet

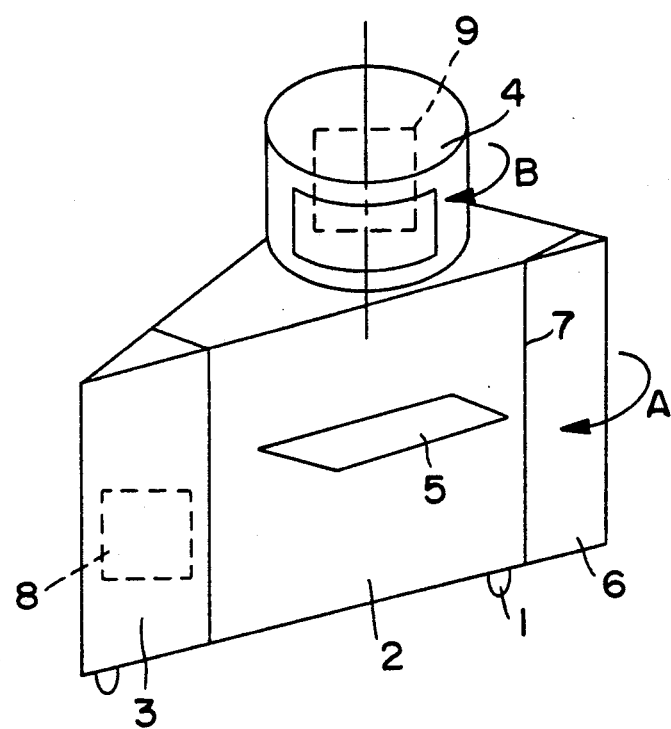

RESPIRATING APPARATUS FOR PATIENTS

This application is a continuation of Ser. No. 07/327,870, filed on Mar. 23, 1989, now abandoned.

BACKGROUND OF THE INVENTION

The invention relates to a respirating apparatus for patients, more particularly to be used for anaesthesia, which is formed by a housing with means for forming and administering of a respiratory gas, and with associated regulating- and control-equipment (monitor) belonging to it.

In the prior art apparatus, the housing in general has the shape of a rectangular parallelepiped, and thus as a rule a rectangular horizontal section. This shape of housing has the disadvantage, that it takes up a relatively large amount of space at the operating table, which could be used more suitably by the surgical staff. Further, the shape of the known apparatus has the disadvantage that the respiratory tubes and suction tubes have to be relatively long, because it is difficult or impossible to move the apparatus with the patient-connections close to the patient.

SUMMARY OF THE INVENTION

The invention obviates these drawbacks of the known apparatus.

The apparatus according to the present is characterized in that the housing substantially has the shape of a prism or a cylinder sector with three sidefaces connected to each other over edge-lines which are parallel to one another. In or near a first corner- or nose part, enclosed by two sidefaces, the connecting means 8 for the patient have been installed.

Due to the pointed or triangular shape of the apparatus according to the invention, the patient-connections can be brought close to the patient, without negatively influencing the accessibility of the surgical staff to the operating table.

While the first, preferably the most pointed corner or nose part contains the patient-connections, according to a further embodiment of the apparatus according to the invention, both other corner parts are rotatable around vertical rotation axes towards the first corner part and against the sidefaces as designated by arrow A. Due to these features, it is possible upon the turning back of both of these other corner parts to reduce the overall width of the backside of the apparatus, which facilitates the transportation of the apparatus through narrow passages, such as doorways and the like.

In one preferred embodiment of the apparatus according to the invention, the angle formed by the sidefaces which enclose the first corner part or nose part, is between 30 degrees and 60 degrees.

In a preferable embodiment of the invented apparatus, the regulating- and control-equipment has been installed on the housing as a unit, rotatable around a vertical axis, in such a way, that the apparatus is operable by an anesthesiologist from each of the three sidefaces. Accordingly the anaesthetist can perform his work, without hindering the surgical staff in their movements.

The invention will now be explained in more detail with reference to the drawing of an embodiment by way of example.

DESCRIPTION OF THE PREFERRED EMBODIMENTS

As shown schematically in the drawing, the apparatus according to this example of an embodiment has been provided with a housing 2 in the shape of a prism, movable on swivel castors 1, with a sharp nose part or a first corner part 3, that has been provided with connections for the patient 8, such as respiratory tubes, the oxigenation set, the suction tubes, etc.

On the housing the regulating- and control-equipment 9 has been installed in separate enclosure 4, which is rotatable in respect to the housing as indicated by arrow, so that the anaesthetist may operate the apparatus from the backside as well as from the sidefaces which border the nose part 3, and thus may take a position which least hinders the surgical staff. Each sideface of the housing has been provided with a writing plate 5, which can be drawn from out of the housing. Both the back corner parts 6 are rotatable to the front around the vertical axes 7, causing the width of the backside of the housing to be reduced, which facilitates the transportation of the apparatus through narrow passages.

Furthermore, these rotatable back corner parts 6, which may be turned away or out, may serve as storage space for medicine, accessories, bandages, etc.

We claim:

1. A housing for respiratory apparatus for use particularly in the administration of anaesthesia to patients comprising:
    a generally enclosed base portion having a top surface supporting thereon regulating and control apparatus,
    said base portion having generally vertical side-enclosing exterior surfaces, said base portion being so configured that its cross-section over substantially its entire height is substantially triangular,
    two of said vertical side surfaces being joined at substantially vertical edges of said surfaces, said two surfaces forming therebetween in cross-section an acute angle;
    and means connected to said base portion for providing connections between the respiratory apparatus and the patient, said means being connected substantially at the acute angled junction of said two vertical side surfaces to thereby permit said apparatus to be used in close proximity to the patient without substantially interfering with medical personnel attending the patient.

2. The apparatus of claim 1 in which the regulating and control apparatus is housed within a separate enclosure rotatably mounted on the top of said base portion.

3. The apparatus of claim 1 in which said acute angle is between about 30° and about 60°.

4. The apparatus of claim 1 in which said base portion includes a third generally vertical side surface joining said two vertical side surfaces at vertical edges remote from the junction formed between said two vertical side surfaces, and at least one corner part mounted for rotation about a vertical axis located substantially at the junction of said third vertical side surface with an adjoining one of said two vertical side surfaces.

5. The apparatus of claim 4 in which the angle formed between said two vertical surfaces is smaller than the angle formed between either of said two vertical side surfaces with said third vertical side surface.

* * * * *